(12) United States Patent
Hargrove (10) Patent No.: US 12,059,531 B2
(45) Date of Patent: Aug. 13, 2024

(54) NITRIC OXIDE GENERATION, DELIVERY, AND MONITORING SYSTEM

(71) Applicant: ALTI, LLC, Highland Park, IL (US)

(72) Inventor: James McChesney Hargrove, Highland Park, IL (US)

(73) Assignee: ALTI LLC, Highland park, IL (US)

( * ) Notice: Subject to any disclaimer, the term of this patent is extended or adjusted under 35 U.S.C. 154(b) by 706 days.

(21) Appl. No.: 17/341,311

(22) Filed: Jun. 7, 2021

(65) Prior Publication Data
US 2021/0379321 A1 Dec. 9, 2021

Related U.S. Application Data

(60) Provisional application No. 63/035,761, filed on Jun. 7, 2020.

(51) Int. Cl.
*A61M 16/12* (2006.01)

(52) U.S. Cl.
CPC ... *A61M 16/125* (2014.02); *A61M 2202/0208* (2013.01); *A61M 2202/0275* (2013.01); *A61M 2205/3334* (2013.01); *A61M 2205/3368* (2013.01)

(58) Field of Classification Search
CPC .... A61M 16/00–0003; A61M 16/0051; A61M 16/0057; A61M 16/0087–0093; A61M 16/0841–0858; A61M 16/10–1005; A61M 16/105; A61M 16/106; A61M 16/107; A61M 16/1075; A61M 16/12–127; A61M 16/20–203; A61M 2016/003–0033; A61M 2016/102; A61M 2202/0208–0216; A61M 2202/0275; A61M 2205/3334; A61M 2205/3368

See application file for complete search history.

(56) References Cited

U.S. PATENT DOCUMENTS

| | | | |
|---|---|---|---|
| 5,692,495 A | 12/1997 | Sheu | |
| 9,804,138 B2 * | 10/2017 | Brown | G01N 33/0016 |
| 2009/0241947 A1 * | 10/2009 | Bedini | A61M 16/0666 128/203.14 |
| 2011/0240019 A1 * | 10/2011 | Fine | A61M 16/12 128/202.26 |
| 2020/0238041 A1 * | 7/2020 | Zapol | A61M 16/085 |
| 2020/0361772 A1 * | 11/2020 | Hall | H01J 37/32146 |

FOREIGN PATENT DOCUMENTS

CN 1099997 A 3/1995

OTHER PUBLICATIONS

Stenqvist et al. "Evaluation of a new system for ventilatory administration of nitric oxide." Acta Anaesthesiologica Scandinavica. vol. 37, Issue 7, pp. 687-691 (Oct. 1993).
PCT/US2021/036265. International Search Report & Written Opinion (Sep. 22, 2021).

* cited by examiner

*Primary Examiner* — Rachel T Sippel
(74) *Attorney, Agent, or Firm* — Heidi Eisenhut; LOZA & LOZA, LLP (57) ABSTRACT

A method of forming a stream having a therapeutic concentration of nitric oxide (NO) is disclosed, along with an apparatus and system suitable to accomplish this method.

20 Claims, 4 Drawing Sheets

NITRIC OXIDE GENERATION, DELIVERY, AND MONITORING SYSTEM

RELATED APPLICATION

This application claims the benefit of a U.S. Provisional Application Ser. No. 63/035,761 filed Jun. 7, 2020, the disclosure of which is incorporated by reference herein in its entirety.

FIELD OF INVENTION

The instant disclosure generally relates to a method, system and apparatus for producing a stream having a therapeutic concentration of nitric oxide (NO) suitable for delivery to a patient.

NO is known to be useful for treatment of respiratory ailments. However, the formation of NO is difficult, the monitoring of NO is problematic, and the formation of $NO_2$ presents issues due to the toxicity at concentrations over 100 ppb. In addition, exhalation of NO by a patient results in the formation and accumulation of $NO_2$ in the enclosure, i.e., the hospital room, presenting toxicity issues to patient and staff.

There is a need to be able to generate streams having a therapeutic concentration of nitric oxide.

SUMMARY OF INVENTION

This summary is provided to introduce a selection of concepts that are further described below in the detailed description. This summary is not intended to identify key or essential features of the claimed subject matter, nor is it intended to be used as an aid in limiting the scope of the claimed subject matter.

In embodiments, a method of forming a stream having a therapeutic concentration of nitric oxide (NO) comprises providing a first mixture comprising nitric oxide and optionally nitrogen dioxide ($NO_2$) to a mixer; mixing at least a portion of the first mixture with oxygen to produce a second mixture comprising oxygen and nitric oxide; directing at least a portion of the second mixture through at least one analyzer to determine a concentration of nitric oxide or a concentration of nitric oxide and nitrogen dioxide present in the second mixture; and controlling the amount of the first mixture, the oxygen supplied to the mixer, or both to produce a final mixture comprising the therapeutic concentration of nitric oxide and less than or equal to about 100 ppb nitrogen dioxide suitable for delivery to a patient.

In embodiments, the first mixture is produced by providing a mixture of nitrogen and oxygen to an ozone generator to produce a premixture comprising oxygen, nitrogen, ozone and optionally nitrogen oxide and/or nitrogen dioxide and contacting the premixture in a first reactor with a catalyst comprising a metal from one or more of Groups 4 through 12 of the periodic table of elements suitable to convert nitrogen and ozone present in the premixture into the first mixture at a temperature, pressure, and for a period of time sufficient to produce the first mixture, according to the equations:

$$N_2+2O_3 \rightarrow 2NO+2O_2 \text{ and } N_2+O_2 \rightarrow 2NO.$$

In other embodiments, an apparatus comprises an ozone generator having an inlet in fluid communication with a source of nitrogen and oxygen and an outlet in fluid communication with an inlet of a reactor comprising a catalyst comprising a metal from one or more of Groups 4 through 12 of the periodic table of elements suitable to convert nitrogen and ozone present in a first fluid exiting the ozone generator into a second fluid having an increased concentration of nitric oxide relative to the first fluid; an outlet of the reactor in fluid communication with a mixer wherein the second fluid exiting the reactor is mixed with oxygen to produce a third fluid having a therapeutic concentration of nitric oxide and less than about 100 ppb of nitrogen dioxide; and at least one analyzer in fluid communication with the outlet of the mixer suitable to determine a concentration of nitrogen dioxide or a concentration of nitrogen oxide and nitrogen dioxide present in the third fluid.

In still other embodiments is a system comprising one or more embodiments of the apparatus suitable to produce a stream comprising a therapeutic concentration of nitric oxide and less than about 100 ppb of nitrogen dioxide according to one or more embodiments of methods disclosed herein.

DETAILED DESCRIPTION

At the outset, it should be noted that in the development of any such actual embodiment, numerous implementation-specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary and this detailed description, each numerical value should be read once as modified by the term "about" (unless already expressly so modified), and then read again as not so modified unless otherwise indicated in context.

Also, in the summary and this detailed description, it should be understood that a physical range listed or described as being useful, suitable, or the like, is intended that any and every value within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range.

It is to be understood that various embodiments of the present disclosure will be described with reference to the accompanying drawings. Accordingly, those of ordinary skill in the art will recognize that modifications, equivalents, and/or alternatives of the various embodiments described herein can be made without departing from the scope and spirit of the present disclosure. With regard to description of drawings, similar components may be marked by similar reference numerals.

For use herein, the expressions "have", "may have", "include", "comprise", "may include", and "may comprise" indicate the existence of corresponding features (e.g., such as numeric values, functions, operations, or components) but do not exclude the presence of additional features.

In the present disclosure, expressions such as, "A and/or B", "at least one of A and/or B", and "one or more of A and/or B", may include any and all combinations of one or more of the associated listed items. For example, the terms "A and/or B" refers to the case (1) where A is included, (2) where B is included, or (3) where both A and B are included.

Terms such as "first", "second", and the like used herein may refer to various elements of various embodiments of the present disclosure, but do not limit the elements. For example, such terms are used only to distinguish an element from another element and do not limit the order and/or priority of the elements. For example, a first user device and a second user device may represent different user devices irrespective of sequence or importance. For example, without departing from the scope of the present disclosure, a first element may be referred to as a second element, and similarly, a second element may be referred to as a first element.

It will be understood that when an element (for example, a first element) is referred to as being operatively or communicatively "coupled with/to" or "connected to" another element (for example, a second element), it can be directly coupled with/to or connected to the other element or indirectly coupled via an intervening element (for example, a third element) may be present. A component in direct fluid communication with another has an inlet of the second device directly coupled to an outlet of the first device. A component in subsequent fluid communication with another has an inlet of the second device directly coupled to an outlet of the first device through one or more intermediate devices.

As used herein, the expressions "configured to", "capable of", "dimensioned to" and the like, used herein may be used interchangeably with, for example, the expression "suitable for", "having the capacity to", "designed to", "adapted to", "made to", or "capable of". The term "configured to (or set to)" does not mean only "specifically designed to" in hardware. Instead, the expression "a device configured to" may mean that the device is "capable of" operating together with another device or other components. For example, an "electronic memory assembly" configured to (or set to) store data for subsequent retrieval, refers to any such memory module or modules, with the associated circuitry, power source, and programming which render it capable of performing the corresponding operation of storage and retrieval utilizing a generic-purpose processor (e.g., a central processing unit (CPU) or an application processor) which may perform corresponding operations by executing one or more software programs which are stored on the memory device.

The various illustrative blocks, modules, flow conduits, and electrical circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read only memory (ROM), flash memory, EPROM memory, EEPROM memory, registers, a hard disk, a removable disk, a CD-ROM and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The controller system refers to a controlling system which typically includes a processor and the related circuitry, valves, flow-meters, and/or other components, e.g., power source, memory, storage, processors, coprocessors, gates, relays, other integrated circuits, software, and/or the like, necessary for its function. The processor may be responsible for managing general processing, including the execution of software stored on a machine-readable media. The processor may be implemented with one or more general-purpose and/or special-purpose processors. Examples include microprocessors, microcontrollers, DSP processors, and other circuitry that can execute software. Software shall be construed broadly to mean instructions, data, or any combination thereof, whether referred to as software, firmware, middleware, microcode, hardware description language, or otherwise. Machine-readable media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may comprise a computer-readable medium having instructions stored (and/or encoded) thereon, the instructions being executable by one or more processors to perform the operations described herein and be embodied in a computer-program product. The computer-program product may comprise packaging materials to advertise the computer-readable medium therein for purchase by consumers.

Computer readable medium may also include, by way of example, a carrier wave, a transmission line, and any other suitable medium for transmitting software and/or instructions that may be accessed and read by a computer or the processor. The non-transient computer readable medium may reside in the device, external to the device, or distributed across multiple entities including the device. The non-transient computer readable medium may be embodied in a computer program product. By way of example, a computer program product may include a computer readable medium in packaging materials. Those skilled in the art will recognize how best to implement the described functionality presented throughout this disclosure depending on the particular application and the overall design constraints imposed on the overall system.

Within the present disclosure, the word "exemplary" and/or "preferably" are used to mean "serving as an example, instance, or illustration." Any implementation or aspect described herein as "exemplary" and/or "preferably" are is not necessarily to be construed as preferred or advantageous over other aspects of the disclosure in an overall limiting sense, but only in relation to specific embodiments. Likewise, the term "aspects" does not require that all aspects of the disclosure include the discussed feature, advantage or mode of operation. The term "coupled" is used herein to refer to the direct or indirect coupling between two objects. For example, if object A physically touches object B, and object B touches object C, then objects A and C may still be considered coupled to one another—even if they do not directly physically touch each other. For instance, a first object may be coupled to a second object even though the first object is never directly physically in contact with the second object. The terms "circuit" and "circuitry" are used broadly, and intended to include both hardware implementations of electrical devices and conductors that, when connected and configured, enable the performance of the functions described in the present disclosure, without limitation as to the type of electronic circuits, as well as software implementations of information and instructions that, when executed by a processor, enable the performance of the functions described in the present disclosure.

One or more of the components, steps, features and/or functions illustrated in the figures may be rearranged and/or combined into a single component, step, feature or function or embodied in several components, steps, or functions. Additional elements, components, steps, and/or functions may also be added without departing from novel features disclosed herein. The apparatus, devices, and/or components illustrated in the figures may be configured to perform one or more of the methods, features, or steps described herein. The novel algorithms described herein may also be efficiently implemented in software and/or embedded in hardware.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order and are not meant to be limited to the specific order or hierarchy presented unless specifically recited therein.

The terms used herein are used to describe specific embodiments of the present disclosure and are not intended to limit the scope of the present disclosure. The terms of a singular form may include plural forms unless otherwise specified. Unless otherwise defined herein, all the terms used herein, which include technical or scientific terms, may have the same meaning as that generally understood by a person skilled in the art to which the present disclosure pertains. It will be further understood that terms, which are defined in a dictionary and commonly used, should also be interpreted as is customary in the relevant related art and not in an idealized or overly formal manner unless expressly so defined herein. In some cases, even if terms are defined in the specification, they may not be interpreted to exclude embodiments of the present disclosure.

In various embodiments of the present disclosure, the components referred to in embodiments of the device is not limited to currently known devices but may include new devices suitable for the intended purpose which are subsequently produced due to the development of new technologies.

As used herein, the term "determining" and "conversion" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Furthermore, "determining" may include resolving, selecting, choosing, establishing and the like. Likewise, "controlling" encompasses a wide variety of actions, the totality of which results in the functioning of the device for the intended purpose.

The following detailed description is of the best currently contemplated modes of carrying out the invention. The description is not to be taken in a limiting sense, but is made merely for the purpose of illustrating the general principles of the invention.

In embodiments, a method of forming a stream having a therapeutic concentration of nitric oxide (NO) comprises providing a first mixture comprising nitric oxide and optionally nitrogen dioxide ($NO_2$) to a mixer; mixing at least a portion of the first mixture with oxygen to produce a second mixture comprising oxygen and nitric oxide; directing at least a portion of the second mixture through at least one analyzer to determine a concentration of nitric oxide or a concentration of nitric oxide and nitrogen dioxide present in the second mixture; and controlling the amount of the first mixture, the oxygen supplied to the mixer, or both to produce a final mixture comprising the therapeutic concentration of nitric oxide and less than or equal to about 100 ppb nitrogen dioxide suitable for delivery to a patient. In some embodiments the first mixture is produced by providing a mixture of nitrogen and oxygen to an ozone generator to produce a premixture comprising oxygen, nitrogen, ozone and optionally nitrogen oxide and/or nitrogen dioxide; contacting the premixture in a first reactor with a catalyst comprising a metal from one or more of Groups 4 through 12 of the periodic table of elements suitable to convert nitrogen and ozone present in the premixture into the first mixture at a temperature, pressure, and for a period of time sufficient to produce the first mixture, wherein the first mixture comprises a concentration of nitric oxide greater than a concentration of nitric oxide present, if any, in the premixture.

In some embodiments, the mixture of nitrogen and oxygen provided to the ozone generator comprises air. In embodiments, the method further comprises controlling the flow of nitrogen, oxygen, and/or air into the ozone generator, the temperature of the first reactor, an output of the ozone generator, a flowrate of the premixture, a residence time in the first reactor, or a combination thereof, to produce the final mixture.

In embodiments, the first reactor comprises a catalyst comprising chromium, copper, iron, molybdenum, nickel, or a combination thereof at a temperature of greater than or equal to about 250° C., or greater than or equal to about 350°

C., or greater than or equal to about 400° C. In embodiments, the temperature is less than or equal to about 500° C. In embodiments, the reactor is at or near ambient pressure, and has a residence time of greater than or equal to about 0.5 seconds.

In one or more embodiments, method further comprises i) directing the first mixture through a nitrogen dioxide trap at a temperature and for a period of time sufficient reduce a concentration of nitrogen dioxide present, if any, in the first mixture; ii) directing the second mixture through a nitrogen dioxide trap at a temperature and for a period of time sufficient reduce a concentration of nitrogen dioxide present, if any, in the second mixture; or a combination thereof.

In embodiments, the nitrogen dioxide trap comprises calcium hydroxide.

Preferably the nitrogen dioxide trap comprise Actinite B, a combination of calcium hydroxide and glycerine on a support.

In embodiments, the least one analyzer comprises an electrochemical sensor, an infrared spectrometer, a near-infrared spectrometer, a UV-VIS spectrometer, a photoacoustic spectrometer, and/or a cavity ring down spectrometer.

In embodiments, the at least one analyzer comprises a first analyzer and a second analyzer. In some embodiments, at least a portion of the second mixture is directed through a first analyzer to determine the concentration of nitrogen dioxide in the final mixture, and that portion or another portion of the second mixture is directed through a second analyzer to determine the concentration of nitric oxide in the final mixture.

In embodiments, the first analyzer and/or the second analyzer (when present) comprises a cavity ring down spectrometer.

In embodiments, the determination of the nitric oxide concentration comprises the steps of contacting the portion of the second mixture in a second reactor comprising a catalyst with an amount of ozone at a temperature, pressure and for a period of time sufficient to convert the nitric oxide present into nitrogen dioxide, to produce a third mixture, followed by directing the third mixture into a the second analyzer to determine an nitrogen dioxide concentration in the third mixture, and conversion of the nitrogen dioxide concentration in the third mixture into the nitric oxide concentration in the final mixture.

In embodiments, a single analyzer determines the concentration of nitrogen oxide and nitrogen dioxide present in the second mixture. In some embodiments, the single analyzer comprises two or more analysis pathways, wherein the concentration of nitric oxide is determined in a first analysis pathway and the concentration of nitrogen dioxide is determined in a second analysis pathway either simultaneously or sequentially within the singe analyzer.

In embodiments, the final mixture has a nitric oxide concentration of greater than or equal to about 1 ppm and less than or equal to about 20 ppm and a nitrogen dioxide concentration of less than or equal to about 10 ppb, preferably less than or equal to about 1 ppb.

In some embodiments, the method further comprises directing the final mixture into a gas inhaled by a patient within an enclosure, followed by directing exhaled gas from the patient into a nitric oxide/nitrogen dioxide trap, and/or directing the exhaled gas from the patient into an atmosphere external to the enclosure.

In embodiments, the method further comprises monitoring a concentration of nitric oxide and/or nitrogen dioxide within the enclosure using an enclosure analyzer.

In such embodiments, the enclosure analyzer comprises an electrochemical sensor, an infrared spectrometer, a near-infrared spectrometer, a UV-VIS spectrometer, a photoacoustic spectrometer, and/or a cavity ring down spectrometer.

In one or more embodiments, an apparatus comprises an ozone generator having an inlet in fluid communication with a source of nitrogen and oxygen and an outlet in fluid communication with an inlet of a reactor comprising a catalyst comprising a metal from one or more of Groups 4 through 12 of the periodic table of elements suitable to convert nitrogen and ozone present in a first fluid exiting the ozone generator into a second fluid having an increased concentration of nitric oxide relative to the first fluid; an outlet of the reactor in fluid communication with a mixer wherein the second fluid exiting the reactor is mixed with oxygen to produce a third fluid having a therapeutic concentration of nitric oxide and less than about 100 ppb of nitrogen dioxide; and at least one analyzer in fluid communication with the outlet of the mixer suitable to determine a concentration of nitrogen dioxide or a concentration of nitrogen oxide and nitrogen dioxide present in the third fluid.

In some embodiments the apparatus further comprises a nitrogen dioxide trap in fluid communication with the outlet of the reactor and an inlet of the mixer suitable to reduce a concentration of nitrogen dioxide present in the second fluid a nitrogen dioxide trap in fluid communication with the outlet of the mixer suitable to reduce a concentration of nitrogen dioxide present in the third fluid; or a combination thereof.

In one or more embodiments the apparatus further comprises one or more components selected from the group consisting of: a flow controller of the source of nitrogen and oxygen supplied to the ozone generator, a flow controller of the first fluid, a flow controller of the second fluid, a flow controller of the third fluid, a flow controller of the oxygen supplied to the mixer, a reactor heater, a mixer proportioning assembly, an ozone output controller, and a combination thereof; and a controller electronically coupled to the at least one analyzer and to at least one component capable of controlling at least one component based on a concentration of nitrogen oxide and/or nitrogen dioxide present in the third fluid; to produce the third fluid comprising a therapeutic concentration of nitric oxide and less than about 100 ppb nitrogen dioxide suitable for delivery to a patient.

In some of such embodiments, the apparatus further comprising an enclosure analyzer comprising at least one analyzer in fluid communication with an enclosure in which a patient is located, suitable to determine a concentration of nitrogen dioxide or a concentration of nitrogen oxide and nitrogen dioxide present in the enclosure.

Reactor

In embodiments, the contacting of the mixture with the catalyst to produce the first mixture comprises directing the premixture, typically air, but it could also be nitrogen and oxygen in a particular ratio, through a tubular reactor in which the catalyst is actually the walls of the reactor. In such an embodiment, a metal tube comprising an alloy comprising chromium, copper, iron, molybdenum, nickel, or a combination thereof may be used. Suitable materials include molybdenum containing Monel and other materials known in the art. The walls of the reactor are heated to a temperature of greater than or equal to about 250° C., preferably greater than or equal to about 350° C. although the temperature rise of the gas flowing therethrough is substantially lower. The gas is introduced at ambient pressure, which is only slightly above atmospheric pressure due to the pumping of air into the ozone generator or slightly below atmospheric pressure if the fluid is pulled through the apparatus. The residence time of the gas within the heated reactor is typically greater than or equal to about 0.1 seconds, or greater than or equal to about 0.5 seconds, or greater than or equal to about 1 second, or greater than or equal to about 2 seconds. In embodiments the residence time is less than or equal to about 1 minute.

In embodiments the reactor may include static mixers and/or the catalyst may be in the form of a metal sponge or supported on an inorganic substrate. It may also be in the form of metallic beads through which the first mixture is directed through. In embodiments, the reactor is a metal tube having an inlet portions, a middle portions, and an outlet portion, which is only heated about the inlet portion and/or the middle portion. For example, in an embodiment, the reactor is a 10 cm metal tube of a molybdenum/nickel alloy which is only heated from about 2 cm to about 5 cm from the inlet of the tube.

Analyzers

In embodiments, the method further comprises directing a portion of the first mixture and/or a portion of the second mixture, i.e., a slip stream, into a first analyzer to determine a concentration of $NO_2$ in the second mixture. Since the concentrations of $NO_2$ are very low, typically less than 1 ppb, the first analyzer may comprise a cavity ring down spectrometer. Other suitable analyzers include electrochemical sensors, infrared spectrometers, near-infrared spectrometers, UV-VIS spectrometers, and/or photoacoustic spectrometers. However, if has been discovered that a cavity ring down spectrometer with a path length on the order of about 200 m or greater is sufficient, robust and stable in use.

In embodiments, the portion of the second mixture and/or a portion of the third mixture is directed into a second analyzer to determine an NO concentration in the third mixture.

In embodiments, the determination of the NO concentration may be determined directly using electrochemical sensors, infrared spectrometers, near-infrared spectrometers, UV-VIS spectrometers, and/or photoacoustic spectrometers. In embodiments, infrared spectroscopy is well suited for use since concentrations of both NO and $NO_2$ may be determined simultaneously. UV-Vis spectroscopy may also be used to determine NO directly e.g., NO has a strong absorption at ~226 n. In other embodiments, the determination of NO may be accomplished by converting the NO into $NO_2$ by reacting with ozone in a second reactor, then analyzing for $NO_2$ via visible spectroscopy at ~405 nm. Accordingly, in embodiments, the method comprises the steps of contacting the portion of the second mixture in a second reactor with an amount of ozone at a temperature and for a period of time sufficient to convert the NO present into $NO_2$, to produce a third mixture, followed by flow-through spectroscopic analysis of the reacted third mixture to determine an $NO_2$ concentration in the reacted third mixture. The concentration of NO present in the second mixture is then calculated by conversion of the $NO_2$ concentration in the third mixture into the NO concentration in the second mixture.

In embodiments, this flow through spectroscopic analysis comprises flow through Visible analysis, typically at about 405 nm with a 15 cm path length according to standard methods known in the art. In such embodiments, the ozone utilized for this process must be essentially free from nitrogen and other contaminants. Accordingly, the ozone is produced by a separate ozone generator (not the initial ozone generator) capable of producing reagent grade ozone. Examples include electrolytic ozone production from purified water. Other examples include silent discharge ozone generators, UV ozone generators, and the like.

Controllers

In embodiments, the method further comprises controlling the flow of ambient air (and/or a mixture of nitrogen and oxygen) into the ozone generator, and/or a proportion of the first mixture to the oxygen gas, relative to the concentration of NO obtained from the analyzer, and/or the $NO_2$ concentration determined by the analyzer. This is then directed through the mixer and combined with oxygen, e.g., house oxygen from an independent source, to produce the second mixture having an NO concentration of greater than or equal to about 1 ppm, and an $NO_2$ concentration of less than about 100 ppb, preferably less than or equal to about 50 ppb, preferably less than or equal to about 10 ppb, preferably less than or equal to about 5 ppb, preferably less than or equal to about 1 ppb.

This control may be accomplished via controlling one or more components. In embodiments, the components are selected from the group consisting of a flow controller of the source of nitrogen and oxygen (or air) supplied to the ozone generator, a flow controller of the first fluid, a flow controller of the second fluid, a flow controller of the third fluid, a flow controller of the oxygen supplied to the mixer, a temperature controller of the reactor, e.g., a reactor heater, a mixer proportioning assembly, an ozone output controller, e.g., controlling the amount of power provided to the ozone generator, various valves, vents, recycle valves and other temperatures, e.g., the temperature of any nitrogen dioxide traps, and combinations thereof. The controller is electronically coupled to the at least one analyzer and to at least one component capable of controlling at least one of the components present in the apparatus based on a concentration of nitrogen oxide and/or nitrogen dioxide present in the third fluid; to produce the third fluid comprising a therapeutic concentration of nitric oxide e.g., from about 1 ppm to about 20 ppm, and less than about 100 ppb nitrogen dioxide suitable for delivery to a patient.

The controller then controls the flow meters, recycle streams e.g., via valves, the proportional mixer, and/or the like according to techniques known in the art.

In embodiments, the controlling thus involves a control system in electrical communication with the analyzers, valves, metering pumps, and the like. The controller system further includes computer control comprising a processor and the related circuitry, valves, flow-meters, and/or other components, e.g., power source, memory, storage, processors, coprocessors, gates, relays, other integrated circuits, software, and/or the like, necessary for its function. The processor may be responsible for managing general processing, including the execution of software stored on a machine-readable media. The processor may be implemented with one or more general-purpose and/or special-purpose processors. Examples include microprocessors, microcontrollers, DSP processors, and other circuitry that can execute software. Software shall be construed broadly to mean instructions, data, or any combination thereof, whether referred to as software, firmware, middleware, microcode, hardware description language, or otherwise. Machine-readable media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may comprise a computer-readable medium having instructions stored (and/or encoded) thereon, the instructions being executable by one or more processors to perform the operations described herein and be embodied in a computer-program product.

Final Mixture Comprising the Therapeutic Concentration of Nitric Oxide

In embodiments, the final mixture has an NO concentration of greater than or equal to about 1 ppm and less than or equal to about 100 ppm. In some embodiments, the final mixture has an NO concentration of about 1 ppm to about 20 ppm of NO. In embodiments, the final mixture has greater than or equal to about 1 ppm or greater than or equal to about 5 ppm and less than or equal to about 50 ppm, or less than or equal to about 30 ppm, or less than or equal to about 20 ppm NO. These concentrations may be volume to volume, or based on the mass of the NO present relative to the total mass of the stream.

Enclosure

In embodiments, the final mixture is directed into a gas inhaled by a patient within an enclosure, e.g., a breathing cannula of a patient in a hospital or other medical facility, followed by directing exhaled gas from the patient into a $NO/NO_2$ trap, and/or directing the exhaled gas from the patient into an atmosphere external to the enclosure, e.g., outside of the hospital. This prevents the accumulation of toxic levels of $NO_2$ in the patient's room, which pose health risks to both the patient and hospital staff.

In some embodiments, the atmosphere within the patient's room is monitored for the concentration of NO and/or $NO_2$. This information may be integrated into the control system or provide an alarm should levels become hazardous.

In embodiments, the monitoring of the concentration of NO and/or $NO_2$ within the enclosure comprises an electrochemical sensor, an infrared spectrometer, a near-infrared spectrometer, a UV-VIS spectrometer, a photoacoustic spectrometer, and/or a cavity ring down spectrometer, with a cavity ring down spectrometer being preferred in some embodiments.

Figure 1:
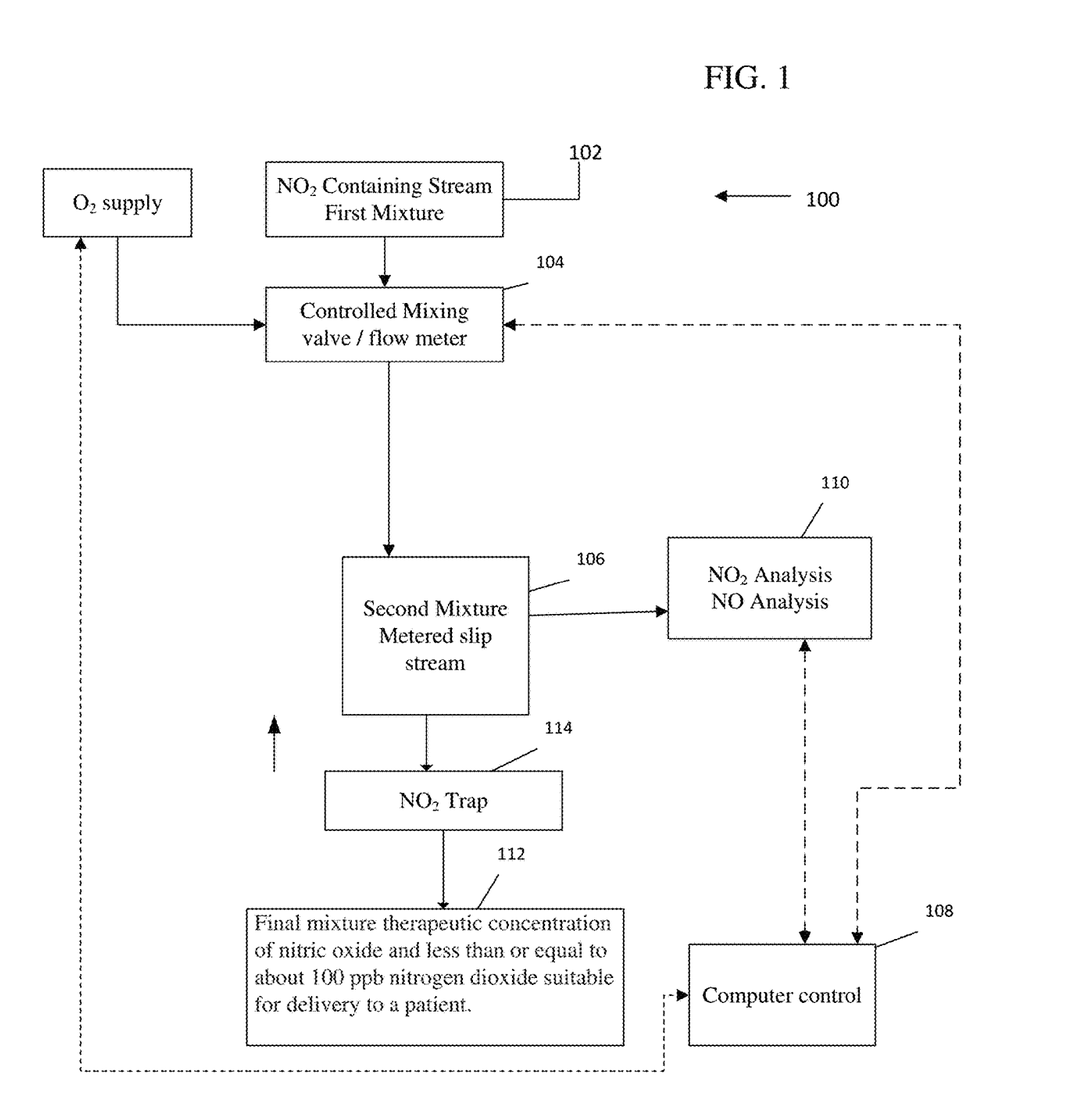
FIG. 1 is a block diagram showing an embodiment of the disclosure.
Figure 2:
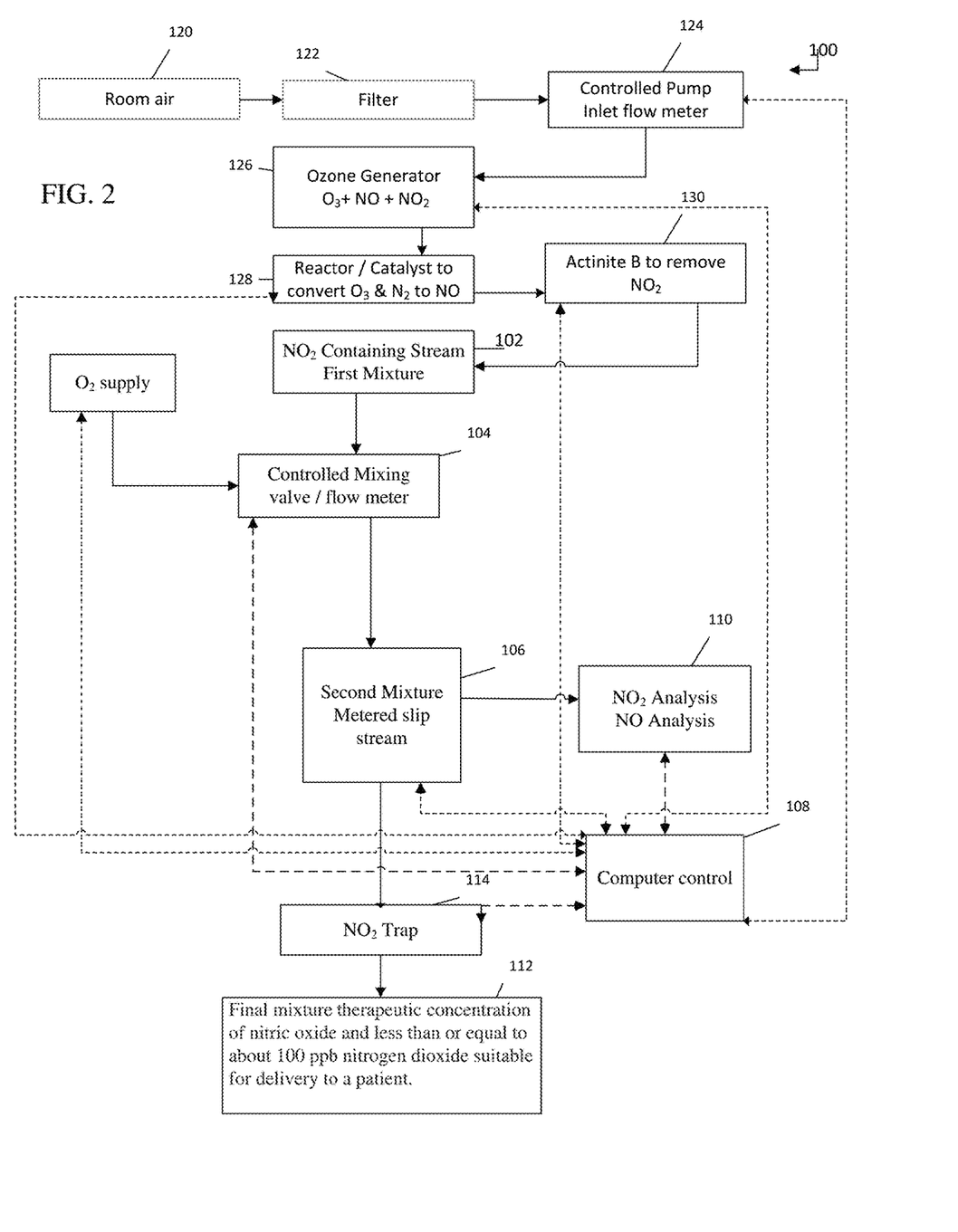
FIG. 2. is a block diagram showing another embodiment according to this disclosure in which an ozone generator is used.

As shown in FIG. 1, in an embodiment method of forming a stream having a therapeutic concentration of nitric oxide (NO), comprises providing a first mixture comprising nitric oxide and optionally nitrogen dioxide ($NO_2$) 102 to a mixer; mixing at least a portion of the first mixture with oxygen (104) to produce a second mixture comprising oxygen and nitric oxide (106). This is followed by directing at least a portion of the second mixture e.g., a slip stream through at least one analyzer (110) to determine a concentration of nitric oxide or a concentration of nitric oxide and nitrogen dioxide present in the second mixture; and controlling the amount of the first mixture, the oxygen supplied to the mixer, or both, with computer control (108) to produce a final mixture comprising the therapeutic concentration of nitric oxide and less than or equal to about 100 ppb nitrogen dioxide suitable for delivery to a patient (112). In the embodiment shown in FIG. 1, the second mixture is directed through a first $NO_2$ trap (114) (e.g., calcium hydroxide) effective to remove $NO_2$ from the stream As shown in FIG. 2, in an embodiment the first mixture is produced by providing a mixture of nitrogen and oxygen (e.g., room air) 120 to an ozone generator 126 to produce a premixture comprising oxygen, nitrogen, ozone and optionally nitrogen oxide and/or nitrogen dioxide. As is shown, the nitrogen and oxygen, which may be room air or compressed air, may be provided to the ozone generator 126 through a filter 122, and may be provided by a metering pump or flow controller 124. The first premixture is then contacted in a first reactor with a catalyst 128 comprising a metal from one or more of Groups 4 through 12 of the periodic table of elements suitable to convert nitrogen and ozone present in the premixture into the first mixture at a temperature, pressure, and for a period of time sufficient to produce the first mixture. In embodiments, the metal comprises chromium, copper, iron, molybdenum, nickel, or a combination thereof, with a combination comprising molybdenum and nickel being preferred. This produces a first mixture comprising a concentration of nitric oxide greater than a concentration of nitric oxide present, if any, in the premixture. As is shown in the figure, the first mixture may be directed through a second $NO_2$ trap 130 to remove $NO_2$ from the mixture.

In embodiments, the inlet flow pump or flow meter may be controlled by the controller, as well as the reactor temperature, the ozone generator, and the temperature of the $NO_2$ trap.

Figure 3:
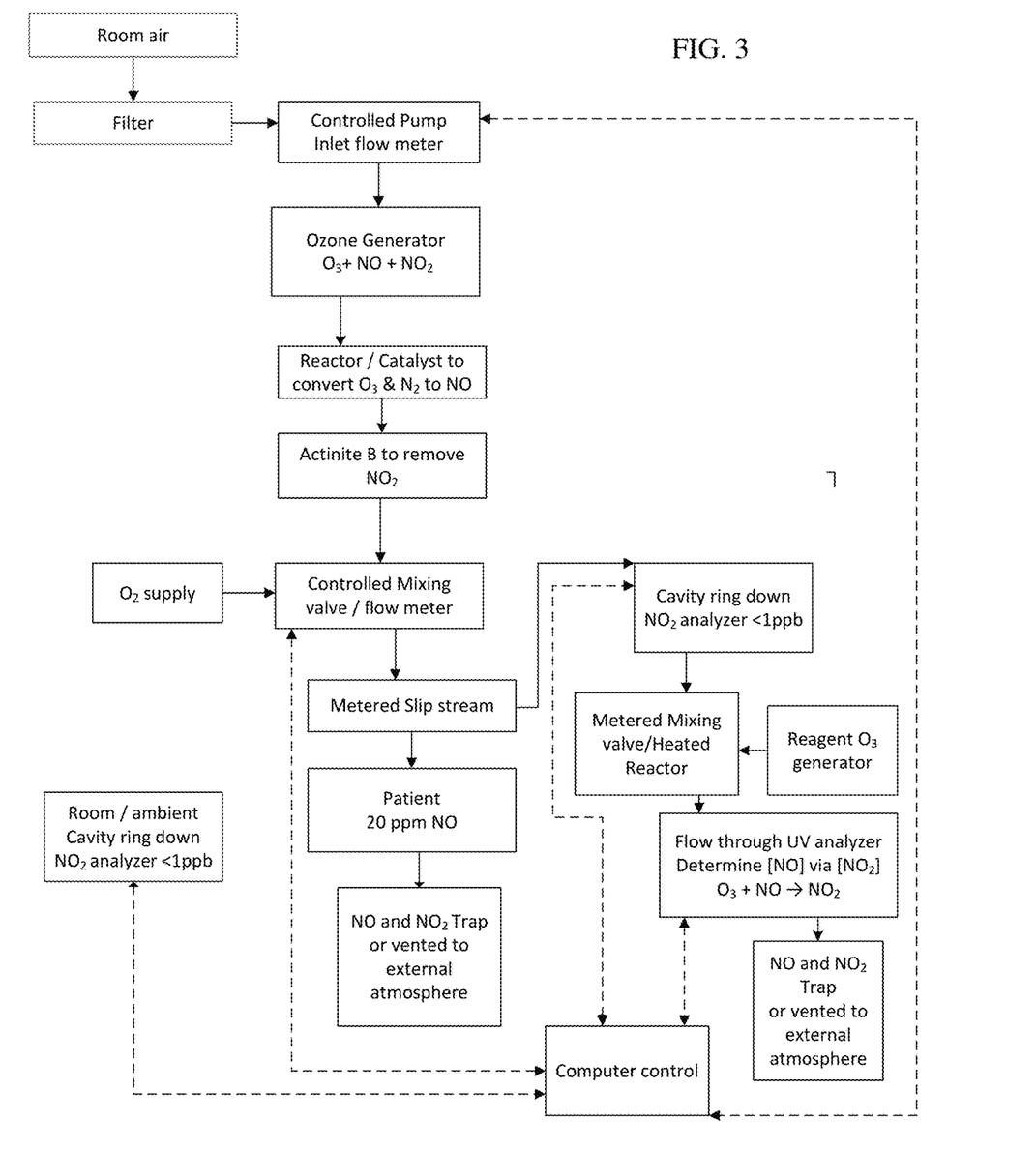
FIG. 3. is a block diagram showing another embodiment according to this disclosure in which the NO is determined by reaction with ozone.

As shown in FIG. 3, in embodiments the method and the accompanying apparatus comprises an ozone generator having an inlet in fluid communication with ambient air and an outlet in fluid communication with an inlet of a reactor comprising a catalyst comprising a metal from one or more of Groups 4 through 12 of the periodic table of elements suitable to convert nitrogen ($N_2$) and ozone ($O_3$) present in a first fluid exiting the ozone generator into a second fluid having an increased concentration of nitric oxide (NO) relative to the first fluid; an outlet of the reactor in fluid communication with a mixer wherein the second fluid exiting the reactor is mixed with oxygen to produce a third fluid having a therapeutic concentration of nitric oxide (NO).

In embodiments, the reactor comprises a metal tube comprising an alloy comprising chromium, copper, iron, molybdenum, nickel, or a combination thereof, heatable to a temperature of greater than or equal to about 250° C., preferably 350° C., and dimensioned to have a residence time of greater than or equal to about 0.5 seconds relative to a flow of the first fluid from the ozone generator.

In some embodiments, the apparatus further comprises an $NO_2$ trap in fluid communication with the outlet of the reactor and an inlet of the mixer suitable to reduce a concentration of $NO_2$ present in the second fluid, if any, prior to mixing with oxygen to produce the third fluid. In embodiments, the $NO_2$ trap comprises calcium hydroxide, which in some embodiments is Actinite B.

In embodiments, a first analyzer is in fluid communication with a portion of the second fluid and/or a portion of the third fluid, which is directed there through to determine a concentration of $NO_2$ in the third fluid, hi embodiments, this first analyzer comprises a cavity ring down spectrometer.

As shown, in embodiments a second analyzer is used to analyze a portion of the second fluid and/or a portion of the third fluid (shown in the FIGs.) which is directed through the analyzer to determine a concentration of NO in the third fluid.

Figure 4:
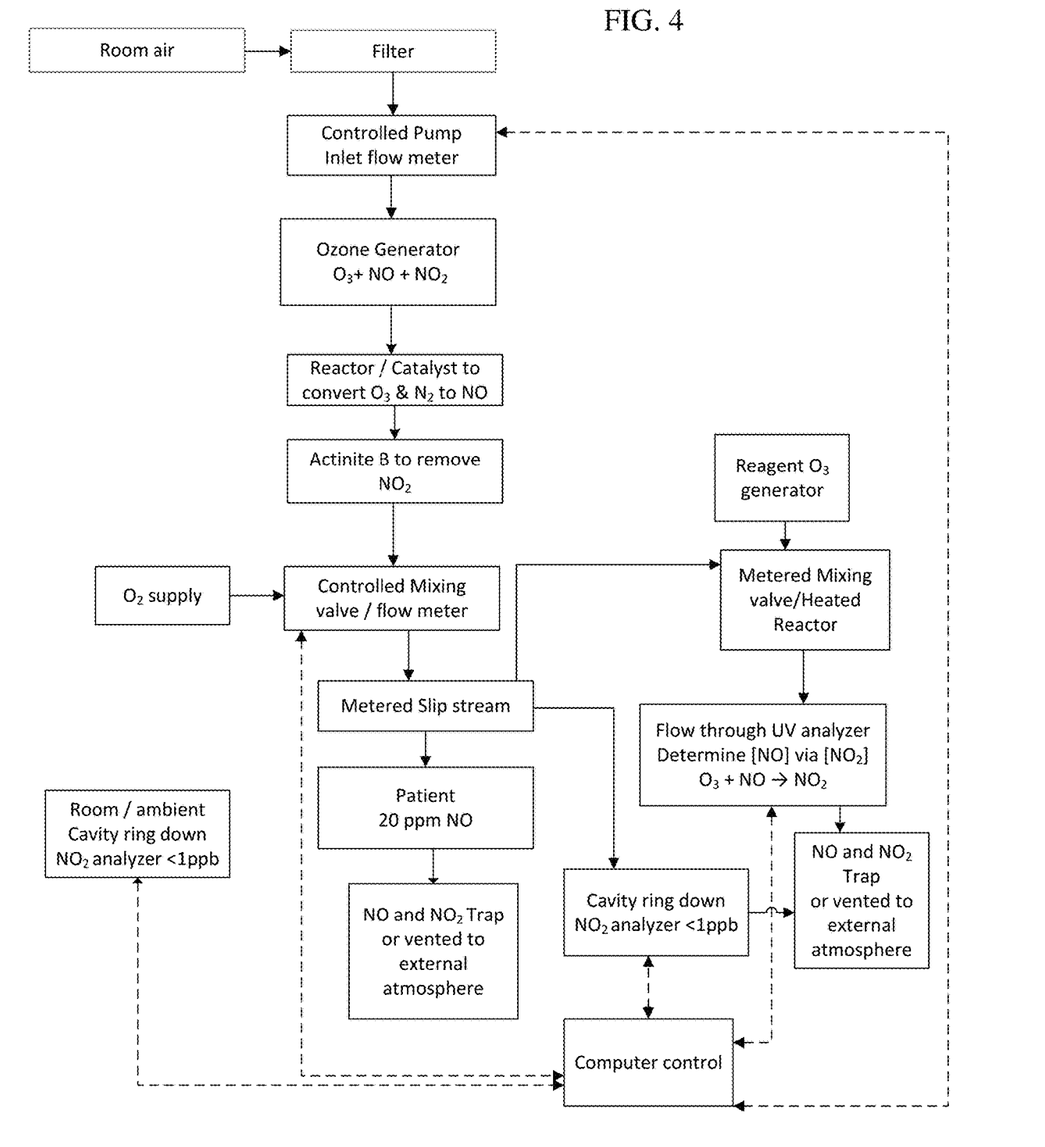
FIG. 4 is a block diagram according to an alternative embodiment of the invention.

As shown in FIG. 4, in embodiments, the portion of the third fluid exiting the first analyzer Is utilized by the second analyzer to determine the concentration of NO In the third fluid.

In embodiments, the second analyzer further comprises a second reactor in fluid communication with an ozone source, suitable to contact the portion of the second fluid and/or the portion of the third fluid with ozone at a temperature, and for a period of time sufficient to convert NO present in the third fluid into $NO_2$, to produce a reacted third fluid, followed by flow-through spectroscopic analysis of the reacted third fluid to determine an $NO_2$ concentration in the reacted third fluid, and conversion of the $NO_2$ concentration in the reacted third fluid into the NO concentration in the third fluid. In embodiments, the flow through spectroscopic analysis comprises flow through UV analysis, preferably at about 405 nm, and the ozone source is a second ozone generator capable of producing reagent grade ozone.

In embodiments, the apparatus further comprises a controller system in electrical communication (dotted lines) with the analyzers and the various components of the apparatus such that it is capable of controlling the flow of ambient air into the ozone generator, and/or a proportion of the second fluid to the oxygen gas, relative to the concentration of NO obtained from the first analyzer, and/or the $NO_2$ concentration determined by the second analyzer to produce the third fluid having an NO concentration of greater than or equal to about 1 ppm, and an $NO_2$ concentration of less than about 1 ppb.

The apparatus of is preferably capable of producing a treatment fluid having an NO concentration of greater than or equal to about 1 ppm and less than or equal to about 100 ppm, or 50 ppm or 20 ppm.

In embodiments, the apparatus or an associated system further comprises an inlet assembly directing the third fluid into a gas inhaled by a patient within an enclosure, and an outlet assembly directing exhaled gas from the patient into a NO/$NO_2$ trap, and/or directing the exhaled gas from the patient into an atmosphere external to the enclosure.

In embodiments, the system further comprises a third analyzer suitable to monitor a concentration of NO and/or $NO_2$ within the enclosure, preferably comprising a cavity ring down spectrometer.

Accordingly, in embodiments room air is filtered so that dust and debris are not introduced. Then an optional capacitance breakdown type ozone generator can be used to make ozone and or nitrogen dioxide ($NO_2$) and other higher oxides of nitrogen (NOy). Then a heater containing a catalyst that includes chromium, copper, iron, molybdenum and/or nickel heated to about 350° C. is used to convert oxygen and nitrogen to nitric oxide with a potential boost from the ozone and NOx of the ozone generator. A metering pump and/or flow-meter could be used to vary the amount of nitric oxide that is generated.

Any $NO_2$ present after the reactor can be removed from this stream as a precaution using a trap, preferably using an Actinite B as the sorbent. This NO rich stream is then introduced into a stream of oxygen provided by the hospital. The stream is sampled by a tee from which a small portion is tested by cavity ring down spectroscopy at 405 nm to determine the $NO_2$ concentration, which must be below a limit that can be set by the operator, preferably less than 1 ppb. The side-stream or another side-stream is then treated with ozone at between about 100° C. and 300° C. to convert the NO to $NO_2$ in a concentration high enough to be detected by a direct single wavelength 405 nm flow through UV analyzer with a roughly 15 cm path-length. This can be used to control the NO concentration to maintain between 1 and 20 ppm supply to the patient, e.g., using a control valve or the inlet pump to the ozone generator can be moderated to achieve the desired concentration, among others.

The NO rich therapeutic stream is then inhaled by the patient according to standard practices. Upon exhalation of the mixture by the patient, the mixture enters a chiller to remove water vapor and is treated ozone at room temperature and trapped in Actinite B or some other sorbent to reduce the risk of poisoning the attendants to the patient. Alternatively, the exhaust can be vented to the outdoors.

In embodiments, when a sufficient volume of NO is inline, if there is a failure of the NO generator in use, the flow of NO may be automatically titrated down by dilution to avoid a sudden reduction in treatment.

In embodiments, the analyzer may include a Cavity Ring Down Spectrometer (CRDS). In one or more embodiments, the analyzer may include a two or more analysis paths from which the second mixture is directed. The first path being used to detect NO and the second being used to detect $NO_2$. For example, a CRDS may include a single laser source in optical communication with a first detector and a second detector. The first detector being optically isolated from the second detector but in optical communication with the laser through a first analysis flow cell, and the second detector is in optical communication with the laser source through a second flow cell, which again is optically isolated from the first flow cell. In this way, the concentration of NO and $NO_2$ may be determined either simultaneously or in succession via gated analysis. Likewise, the detector utilized to determine the amount of $NO_2$ at ppb levels may be a CRDS, or utilize an IR or NIR mode of analysis with a sufficient optical path length to determine the amount of $NO_2$, and the analyzer utilized to determine the higher concentrations of NO may be a UV-Vis spectrometer.

In one embodiment, the analyzer is a single path IR or NIR analyzer and the concentrations of NO and $NO_2$ are determined simultaneously utilizing different characteristic absorbances, which tend to be sharp, well defined peaks in the gas phase.

In embodiments, the sensor is an $NO_2$ sensor to detect amounts of the material in the final mixture above allowable or dangerous limits. The apparatus is then calibrated with a stand-alone analyzer e.g., flow rates, heaters, power supplied to various components, and then the apparatus is allowed to function without the constant monitoring of NO for a particular period of time. In such an embodiment, a single calibration analyzer may be utilized to calibrate a number of the units.

Embodiments Listing

Accordingly, the present disclosure is directed to and includes one or more of the following embodiments.

E1. A method of forming a stream having a therapeutic concentration of nitric oxide (NO) comprising:
providing a first mixture comprising nitric oxide and optionally nitrogen dioxide (NO2) to a mixer;
mixing at least a portion of the first mixture with oxygen to produce a second mixture comprising oxygen and nitric oxide;
directing at least a portion of the second mixture through at least one analyzer to determine a concentration of nitric oxide or a concentration of nitric oxide and nitrogen dioxide present in the second mixture; and
controlling the amount of the first mixture, the oxygen supplied to the mixer, or both to produce a final mixture comprising the therapeutic concentration of nitric oxide and less than or equal to about 100 ppb nitrogen dioxide suitable for delivery to a patient.

E2. The method according to embodiment E1, wherein the first mixture is produced by providing a mixture of nitrogen and oxygen to an ozone generator to produce a premixture comprising oxygen, nitrogen, ozone and optionally nitrogen oxide and/or nitrogen dioxide;

contacting the premixture in a first reactor with a catalyst comprising a metal from one or more of Groups 4 through 12 of the periodic table of elements suitable to convert nitrogen and ozone present in the premixture into the first mixture at a temperature, pressure, and for a period of time sufficient to produce the first mixture, wherein the first mixture comprises a concentration of nitric oxide greater than a concentration of nitric oxide present, if any, in the premixture.

E3. The method according to embodiment E1 or E2, wherein the mixture of nitrogen and oxygen provided to the ozone generator comprises air, and further comprising controlling the flow of nitrogen, oxygen, and/or air into the ozone generator, the temperature of the first reactor, an output of the ozone generator, a flowrate of the premixture, a residence time in the first reactor, or a combination thereof, to produce the final mixture.

E4. The method according to any one of embodiments E1 through E3, wherein the first reactor comprises a catalyst comprising chromium, copper, iron, molybdenum, nickel, or a combination thereof at a temperature of greater than or equal to about 250° C., at or near ambient pressure, and has a residence time of greater than or equal to about 0.5 seconds.

E5. The method according to any one of embodiments E1 through E4, further comprising:
  i) directing the first mixture through a nitrogen dioxide trap at a temperature and for a period of time sufficient reduce a concentration of nitrogen dioxide present, if any, in the first mixture;
  ii) directing the second mixture through a nitrogen dioxide trap at a temperature and for a period of time sufficient reduce a concentration of nitrogen dioxide present, if any, in the second mixture; or a combination thereof.

E6. The method according to embodiment E5, wherein the nitrogen dioxide trap comprises calcium hydroxide.

E7. The method according to any one of embodiments E1 through E6, wherein the at least one analyzer comprises an electrochemical sensor, an infrared spectrometer, a near-infrared spectrometer, a UV-VIS spectrometer, a photoacoustic spectrometer, and/or a cavity ring down spectrometer.

E8. The method according to any one of embodiments E1 through E7, wherein at least a portion of the second mixture is directed through a first analyzer to determine the concentration of nitrogen dioxide in the final mixture, and that portion or another portion of the second mixture is directed through a second analyzer to determine the concentration of nitric oxide in the final mixture.

E9. The method according to any one of embodiments E1 through E8, wherein a first analyzer and/or the second analyzer comprises a cavity ring down spectrometer.

E10. The method according to any one of embodiments E1 through E9, wherein the determination of the nitric oxide concentration comprises the steps of contacting the portion of the second mixture in a second reactor comprising a catalyst with an amount of ozone at a temperature, pressure and for a period of time sufficient to convert the nitric oxide present into nitrogen dioxide, to produce a third mixture, followed by directing the third mixture into a the second analyzer to determine an nitrogen dioxide concentration in the third mixture, and conversion of the nitrogen dioxide concentration in the third mixture into the nitric oxide concentration in the final mixture.

E11. The method according to any one of embodiments E1 through E10, wherein a single analyzer determines the concentration of nitrogen oxide and nitrogen dioxide present in the second mixture.

E12. The method according to any one of embodiments E1 through E11, wherein the single analyzer comprises two or more analysis pathways, wherein the concentration of nitric oxide is determined in a first analysis pathway and the concentration of nitrogen dioxide is determined in a second analysis pathway either simultaneously or sequentially within the singe analyzer.

E13. The method according to any one of embodiments E1 through E12, wherein the final mixture has a nitric oxide concentration of greater than or equal to about 1 ppm and less than or equal to about 20 ppm and a nitrogen dioxide concentration of less than or equal to about 10 ppb.

E14. The method according to any one of embodiments E1 through E13, further comprising directing the final mixture into a gas inhaled by a patient within an enclosure, followed by directing exhaled gas from the patient into a nitric oxide/nitrogen dioxide trap, and/or directing the exhaled gas from the patient into an atmosphere external to the enclosure.

E15. The method according to any one of embodiments E1 through E14, further comprising monitoring a concentration of nitric oxide and/or nitrogen dioxide within the enclosure using an enclosure analyzer.

E16. The method according to any one of embodiments E1 through E15, wherein the enclosure analyzer comprises an electrochemical sensor, an infrared spectrometer, a near-infrared spectrometer, a UV-VIS spectrometer, a photoacoustic spectrometer, and/or a cavity ring down spectrometer.

E17. A method of forming a stream having a therapeutic concentration of nitric oxide (NO) comprising:
  directing ambient air into an ozone generator to form a first mixture comprising nitrogen ($N_2$), oxygen ($O_2$), ozone ($O_3$), nitric oxide (NO) and optionally nitrogen dioxide ($NO_2$) and other higher oxides of nitrogen (NOy), wherein y is greater than or equal to 3;
  contacting the first mixture within a reactor comprising a catalyst comprising a metal from one or more of Groups 4 through 12 of the periodic table of elements at a temperature, pressure, and for a period of time sufficient to produce a second mixture having an increased concentration of NO and a reduced concentration of ozone and nitrogen compared to the first mixture; and
  mixing at least a portion of the second mixture with oxygen to produce a third mixture having a therapeutic concentration of NO suitable for delivery to a patient.

E18. The method according to embodiment E17, wherein the contacting of the first mixture with the catalyst to produce the second mixture comprises directing the first mixture through a metal tube comprising an alloy comprising chromium, copper, iron, molybdenum, nickel, or a combination thereof, at a temperature of greater than or equal to about 250° C., preferably greater than or equal to about 350° C., at ambient pressure and having a residence time of greater than or equal to about 0.5 seconds.

E19 The method according to embodiment E17 or E18, further comprising directing the second mixture through an $NO_2$ trap at a temperature and for a period of time sufficient reduce a concentration of $NO_2$ present in the second mixture, if any, prior to mixing with oxygen to produce the third mixture.

E20. The method according to any one of embodiments E1 through E19, wherein the $NO_2$ trap comprises Actinite B.

E21. The method according to any one of embodiments E17 through E20, further comprising directing a portion of the second mixture and/or a portion of the third mixture into a first analyzer to determine a concentration of $NO_2$ in the third mixture.

E22. The method according to any one of embodiments E17 through E21, wherein the first analyzer comprises a cavity ring down spectrometer.

E23. The method according to any one of embodiments E17 through E22, further comprising directing a portion of the second mixture and/or a portion of the third mixture into a second analyzer to determine an NO concentration in the third mixture.

E24. The method according to any one of embodiments E17 through E23, wherein the determination of the NO concentration comprises the steps of contacting the portion of the third mixture in a second reactor with an amount of ozone at a temperature and for a period of time sufficient to convert the NO present into $NO_2$, to produce a reacted third mixture, followed by flow-through spectroscopic analysis of the reacted third mixture to determine an $NO_2$ concentration in the reacted third mixture, and conversion of the $NO_2$ concentration in the reacted third mixture into the NO concentration in the third mixture.

E25. The method according to any one of embodiments E17 through E24, wherein the flow through spectroscopic analysis comprises flow through LTV analysis.

E26. The method according to any one of embodiments E17 through E25, wherein the ozone is produced by a separate ozone generator capable of producing reagent grade ozone.

E27. The method according to any one of embodiments E17 through E26, further comprising controlling the flow of ambient air into the ozone generator, and/or a proportion of the second mixture to the oxygen gas, relative to the concentration of NO obtained from the first analyzer, and/or the $NO_2$ concentration determined by the second analyzer to produce the third mixture having an NO concentration of greater than or equal to about 1 ppm, and an $NO_2$ concentration of less than about 1 ppb.

E28. The method according to any one of embodiments E17 through E27, wherein the third mixture has an NO concentration of greater than or equal to about 1 ppm and less than or equal to about 20 ppm.

E29. The method according to any one of embodiments E17 through E28, further comprising directing the third mixture into a gas inhaled by a patient within an enclosure, followed by directing exhaled gas from the patient into a $NO/NO_2$ trap, and/or directing the exhaled gas from the patient into an atmosphere external to the enclosure, E30. The method according to any one of embodiments E17 through E29, further comprising monitoring a concentration of NO and/or $NO_2$ within the enclosure.

E31. The method according to any one of embodiments E17 through E30, wherein the monitoring of the concentration of NO and/or $NO_2$ within the enclosure comprises cavity ring down analysis, E32. An apparatus according to any one of embodiments E1 through E31.

E33. An apparatus comprising:
an ozone generator having an inlet in fluid communication with a source of nitrogen and oxygen and an outlet in fluid communication with an inlet of a reactor comprising a catalyst comprising a metal from one or more of Groups 4 through 12 of the periodic table of elements suitable to convert nitrogen and ozone present in a first fluid exiting the ozone generator into a second fluid having an increased concentration of nitric oxide relative to the first fluid;
an outlet of the reactor in fluid communication with a mixer wherein the second fluid exiting the reactor is mixed with oxygen to produce a third fluid having a therapeutic concentration of nitric oxide and less than about 100 ppb of nitrogen dioxide; and
at least one analyzer in fluid communication with the outlet of the mixer suitable to determine a concentration of nitrogen dioxide or a concentration of nitrogen oxide and nitrogen dioxide present in the third fluid.

E34. The apparatus according to embodiment E32 or E33, further comprising a nitrogen dioxide trap in fluid communication with the outlet of the reactor and an inlet of the mixer suitable to reduce a concentration of nitrogen dioxide present in the second fluid;
a nitrogen dioxide trap in fluid communication with the outlet of the mixer suitable to reduce a concentration of nitrogen dioxide present in the third fluid; or a combination thereof.

E35. The apparatus according to any one of embodiments E32 through E34, further comprising one or more components selected from the group consisting of: a flow controller of the source of nitrogen and oxygen supplied to the ozone generator, a flow controller of the first fluid, a flow controller of the second fluid, a flow controller of the third fluid, a flow controller of the oxygen supplied to the mixer, a reactor heater, a mixer proportioning assembly, an ozone output controller, and a combination thereof; and
a controller electronically coupled to the at least one analyzer and to at least one component capable of controlling at least one component based on a concentration of nitrogen oxide and/or nitrogen dioxide present in the third fluid; to produce the third fluid comprising a therapeutic concentration of nitric oxide and less than about 100 ppb nitrogen dioxide suitable for delivery to a patient.

E36. The apparatus according to any one of embodiments E32 through E35, further comprising an enclosure analyzer comprising at least one analyzer in fluid communication with an enclosure in which a patient is located, suitable to determine a concentration of nitrogen dioxide or a concentration of nitrogen oxide and nitrogen dioxide present in the enclosure.

E37. An apparatus comprising:
an ozone generator having an inlet in fluid communication with ambient, air and an outlet in fluid communication with an inlet of a reactor comprising a catalyst comprising a metal from one or more of Groups 4 through 12 of the periodic table of elements suitable to convert nitrogen ($N_2$) and ozone (Os) present in a first fluid exiting the ozone generator into a second fluid having an increased concentration of nitric oxide (NO) relative to the first fluid;
an outlet of the reactor in fluid communication with a mixer wherein the second fluid exiting the reactor is mixed with oxygen to produce a third fluid having a therapeutic concentration of nitric oxide (NO).

E38. The apparatus according to any one of embodiments E32 through E37, wherein the reactor comprises a metal tube comprising an alloy comprising chromium, copper, iron, molybdenum, nickel, or a combination thereof, heatable to a temperature of greater than or equal to about 250° C., preferably 350° C., and dimensioned to have a residence time of greater than or equal to about 0.5 seconds relative to a flow of the first fluid from the ozone generator.

E39. The apparatus according to any one of embodiments E32 through E338, further comprising an $NO_2$ trap in fluid communication with the outlet of the reactor and an inlet of the mixer suitable to reduce a concentration of $NO_2$ present in the second fluid, if any, prior to mixing with oxygen to produce the third fluid.

E40. The apparatus according to any one of embodiments E32 through E339, wherein the $NO_2$ trap comprises Actinite B.

E41. The apparatus according to any one of embodiments E32 through E40, further comprising a first analyzer into which a portion of the second fluid and/or a portion of the third fluid is directed to determine a concentration of $NO_2$ in the third fluid.

E42. The apparatus according to any one of embodiments E32 through E41, wherein the first analyzer comprises a cavity ring down spectrometer.

E43 The apparatus according to any one of embodiments E32 through E42, further comprising a second analyzer into which a portion of the second fluid and/or a portion of the third fluid is directed to determine a concentration of NO in the third fluid.

E44. The apparatus according to any one of embodiments E32 through E43, wherein the portion of the third fluid exiting the first analyzer is utilized by the second analyzer to determine the concentration of NO in the third fluid.

E45. The apparatus according to any one of embodiments E32 through E44, wherein the second analyzer further comprises a second reactor in fluid communication with an ozone source, suitable to contact the portion of the second fluid and/or the portion of the third fluid with ozone at a temperature, and for a period of time sufficient to convert NO present in the third fluid into $NO_2$, to produce a reacted third fluid, followed by flow-through spectroscopic analysis of the reacted third fluid to determine an $NO_2$ concentration in the reacted third fluid, and conversion of the $NO_2$ concentration in the reacted third fluid into the NO concentration in the third fluid.

E46. The apparatus according to any one of embodiments E32 through E445, wherein the flow through spectroscopic analysis comprises flow through UV analysis.

E47. The apparatus according to any one of embodiments E32 through E46, wherein the ozone source is a second ozone generator capable of producing reagent grade ozone.

E48. The apparatus according to any one of embodiments E32 through E47, further comprising a controller system capable of controlling the flow of ambient air into the ozone generator, and/or a proportion of the second fluid to the oxygen gas, relative to the concentration of NO obtained from the first analyzer, and/or the $NO_2$ concentration determined by the second analyzer to produce the third fluid having an NO concentration of greater than or equal to about 1 ppm, and an $NO_2$ concentration of less than about 1 ppb.

E49. The apparatus according to any one of embodiments E32 through E448, wherein the third fluid has an NO concentration of greater than or equal to about 1 ppm and less than or equal to about 20 ppm.

E50. The apparatus according to any one of embodiments E32 through E49, further comprising an inlet assembly directing the third fluid into a gas inhaled by a patient within an enclosure, and an outlet assembly directing exhaled gas from the patient into a $NO/NO_2$ trap, and/or directing the exhaled gas from the patient into an atmosphere external to the enclosure.

E51. The apparatus according to any one of embodiments E32 through E50, further comprising a third analyzer suitable to monitor a concentration of NO and/or $NO_2$ within the enclosure, E52. The apparatus according to any one of embodiments E32 through E51, wherein the third analyzer comprises a cavity ring down spectrometer.

While certain exemplary embodiments have been described and shown in the accompanying drawings, it is to be understood that such embodiments are merely illustrative of and not restrictive on the broad invention, and that this invention is not be limited to the specific constructions and arrangements shown and described, since various other modifications may occur to those ordinarily skilled in the art.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein but are to be accorded the full scope consistent with the language of the claims, wherein reference to an element in the singular is not intended to mean "one and only one" unless specifically so stated, but rather "one or more." Unless specifically stated otherwise, the term "some" refers to one or more.

A phrase referring to "at least one of:" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims.

Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

What is claimed is:

1. A method of forming a stream having a therapeutic concentration of nitric oxide (NO) comprising:
   providing a first mixture comprising nitric oxide and optionally nitrogen dioxide ($NO_2$) to a mixer;
   mixing at least a portion of the first mixture with oxygen to produce a second mixture comprising oxygen and nitric oxide;
   directing at least a portion of the second mixture through at least one analyzer to determine a concentration of nitric oxide or a concentration of nitric oxide and nitrogen dioxide present in the second mixture; and
   controlling the amount of the first mixture, the oxygen supplied to the mixer, or both to produce a final mixture comprising the therapeutic concentration of nitric oxide and less than or equal to about 100 ppb nitrogen dioxide suitable for delivery to a patient,
   wherein the first mixture is produced by providing a mixture of nitrogen and oxygen to an ozone generator to produce a premixture comprising oxygen, nitrogen, ozone and optionally nitrogen oxide and/or nitrogen dioxide;

contacting the premixture in a first reactor with a catalyst comprising a metal from one or more of Groups 4 through 12 of the periodic table of elements suitable to convert nitrogen and ozone present in the premixture into the first mixture at a temperature and pressure, and for a period of time sufficient to produce the first mixture, wherein the first mixture comprises a concentration of nitric oxide greater than a concentration of nitric oxide present, if any, in the premixture.

2. The method of claim 1, wherein the mixture of nitrogen and oxygen provided to the ozone generator comprises air, and further comprising controlling the flow of nitrogen, oxygen, and/or air into the ozone generator, the temperature of the first reactor, an output of the ozone generator, a flowrate of the premixture, a residence time in the first reactor, or a combination thereof, to produce the final mixture.

3. The method of claim 1, wherein the first reactor comprises a catalyst comprising chromium, copper, iron, molybdenum, nickel, or a combination thereof at a temperature of greater than or equal to about 250° C., at or near ambient pressure, and has a residence time of greater than or equal to about 0.5 seconds.

4. The method of claim 1, wherein the at least one analyzer comprises an electrochemical sensor, an infrared spectrometer, a near-infrared spectrometer, a UV-VIS spectrometer, a photoacoustic spectrometer, and/or a cavity ring down spectrometer.

5. The method of claim 1, wherein the at least one analyzer comprises first and second analyzers, and at least a portion of the second mixture is directed through a first analyzer to determine the concentration of nitrogen dioxide in the final mixture, and that portion or another portion of the second mixture is directed through a second analyzer to determine the concentration of nitric oxide in the final mixture.

6. The method of claim 5, wherein the first analyzer and/or the second analyzer comprises a cavity ring down spectrometer.

7. The method of claim 5, wherein the determination of the nitric oxide concentration comprises the steps of contacting the portion of the second mixture in a second reactor comprising a catalyst with an amount of ozone at a temperature and pressure and for a period of time sufficient to convert the nitric oxide present into nitrogen dioxide, to produce a third mixture, followed by directing the third mixture into the second analyzer to determine a nitrogen dioxide concentration in the third mixture, and conversion of the nitrogen dioxide concentration in the third mixture into the nitric oxide concentration in the final mixture.

8. The method of claim 1, wherein the at least one analyzer comprises a single analyzer that determines the concentration of nitric oxide and nitrogen dioxide present in the second mixture.

9. The method of claim 8, wherein the single analyzer comprises two or more analysis pathways, wherein the concentration of nitric oxide is determined in a first analysis pathway and the concentration of nitrogen dioxide is determined in a second analysis pathway either simultaneously or sequentially within the single analyzer.

10. The method of claim 1, wherein the final mixture has a nitric oxide concentration of greater than or equal to about 1 ppm and less than or equal to about 20 ppm and a nitrogen dioxide concentration of less than or equal to about 10 ppb.

11. The method of claim 1, further comprising directing the final mixture into an enclosure, the final mixture then being inhaled by a patient, followed by directing exhaled gas from the patient into a nitric oxide/nitrogen dioxide trap, and/or directing the exhaled gas from the patient into an atmosphere external to the enclosure.

12. The method of claim 11, further comprising monitoring a concentration of nitric oxide and/or nitrogen dioxide within the enclosure using an enclosure analyzer.

13. The method of claim 12, wherein the enclosure analyzer comprises an electrochemical sensor, an infrared spectrometer, a near-infrared spectrometer, a UV-VIS spectrometer, a photoacoustic spectrometer, and/or a cavity ring down spectrometer.

14. A method of forming a stream having a therapeutic concentration of nitric oxide (NO) comprising:
providing a first mixture comprising nitric oxide and optionally nitrogen dioxide ($NO_2$) to a mixer:
mixing at least a portion of the first mixture with oxygen to produce a second mixture comprising oxygen and nitric oxide;
directing at least a portion of the second mixture through at least one analyzer to determine a concentration of nitric oxide or a concentration of nitric oxide and nitrogen dioxide present in the second mixture; and
controlling the amount of the first mixture, the oxygen supplied to the mixer, or both to produce a final mixture comprising the therapeutic concentration of nitric oxide;
directing the first mixture through a first nitrogen dioxide trap at a temperature and for a period of time sufficient to reduce a concentration of nitrogen dioxide present, if any, in the first mixture; and
directing the second mixture through a second nitrogen dioxide trap at a temperature and for a period of time sufficient to reduce a concentration of nitrogen dioxide present, if any, in the second mixture; or a combination thereof.

15. The method of claim 14, wherein the second nitrogen dioxide trap comprises calcium hydroxide.

16. The method of claim 14, wherein the first mixture is produced by providing a mixture of air or a mixture of nitrogen and oxygen to an ozone generator in the presence of a catalyst.

17. An apparatus comprising:
an ozone generator having an inlet in fluid communication with a source of nitrogen and oxygen and an outlet in fluid communication with an inlet of a reactor comprising a catalyst comprising a metal from one or more of Groups 4 through 12 of the periodic table of elements suitable to convert nitrogen and ozone present in a first fluid exiting the ozone generator into a second fluid having an increased concentration of nitric oxide relative to the first fluid;
an outlet of the reactor in fluid communication with a mixer wherein the second fluid exiting the reactor is mixed with oxygen to produce a third fluid having a therapeutic concentration of nitric oxide and less than about 100 ppb of nitrogen dioxide; and
at least one analyzer in fluid communication with the outlet of the mixer suitable to determine a concentration of nitrogen dioxide or a concentration of nitric oxide and nitrogen dioxide present in the third fluid.

18. The apparatus of claims 17, further comprising a nitrogen dioxide trap in fluid communication with the outlet of the reactor and an inlet of the mixer suitable to reduce a concentration of nitrogen dioxide present in the second fluid;
a nitrogen dioxide trap in fluid communication with the outlet of the mixer suitable to reduce a concentration of nitrogen dioxide present in the third fluid; or a combination thereof.

19. The apparatus of claim 17, further comprising:
one or more components selected from the group consisting of: a flow controller of the source of nitrogen and oxygen supplied to the ozone generator, a flow controller of the first fluid, a flow controller of the second fluid, a flow controller of the third fluid, a flow controller of the oxygen supplied to the mixer, a reactor heater, a mixer proportioning assembly, an ozone output controller, and a combination thereof; and
a controller electronically coupled to the at least one analyzer and to at least one component capable of controlling at least one component based on a concentration of nitrogen oxide and/or nitrogen dioxide present in the third fluid; to produce the third fluid comprising a therapeutic concentration of nitric oxide and less than about 100 ppb nitrogen dioxide suitable for delivery to a patient.

20. The apparatus of claim 17 further comprising an enclosure analyzer comprising at least one analyzer in fluid communication with an enclosure in which a patient is located, suitable to determine a concentration of nitrogen dioxide or a concentration of nitrogen oxide and nitrogen dioxide present in the enclosure.

\* \* \* \* \*